United States Patent
Sterling (10) Patent No.: US 9,826,812 B2
(45) Date of Patent: Nov. 28, 2017

(54) WEFTED HAIR DRYER

(71) Applicant: Jody Abram Williams Sterling, Long Beach, CA (US)

(72) Inventor: Jody Abram Williams Sterling, Long Beach, CA (US)

(*) Notice: Subject to any disclaimer, the term of this patent is extended or adjusted under 35 U.S.C. 154(b) by 0 days.

(21) Appl. No.: 15/194,043

(22) Filed: Jun. 27, 2016

(65) Prior Publication Data

US 2016/0374447 A1 Dec. 29, 2016

Related U.S. Application Data (60) Provisional application No. 62/186,305, filed on Jun. 29, 2015.

(51) Int. Cl.
*A45D 20/08* (2006.01)
*A61L 2/10* (2006.01)
*A45D 44/02* (2006.01)

(52) U.S. Cl.
CPC ............ *A45D 20/08* (2013.01); *A45D 44/02* (2013.01); *A61L 2/10* (2013.01); *A61L 2202/21* (2013.01)

(58) Field of Classification Search
CPC ... A45D 20/08; A45D 20/12; A45D 2020/128
USPC ................ 34/275, 96–100; 132/108, 110
See application file for complete search history.

(56) References Cited

U.S. PATENT DOCUMENTS

| | | | | |
|---|---|---|---|---|
| 6,640,049 B1* | 10/2003 | Lee | ............... | A45D 20/08 34/96 |
| 7,047,660 B2* | 5/2006 | Leventhal | ............. | A45D 20/122 34/97 |
| 7,946,056 B2* | 5/2011 | Kroll | ............... | A45D 20/22 132/233 |
| 8,448,349 B2* | 5/2013 | Kloeppel-Riech | ..... | A45D 20/12 132/272 |
| 8,973,284 B2* | 3/2015 | Shami | ............. | A45D 20/12 34/275 |
| 9,498,039 B2* | 11/2016 | Wu | ............... | H01T 23/00 |
| 2009/0078800 A1* | 3/2009 | Nakasone | ............. | A45D 20/12 239/690 |
| 2014/0325863 A1 | 11/2014 | Blum | | |
| 2017/0112257 A1* | 4/2017 | Bobillier | ............. | A45D 20/12 |

FOREIGN PATENT DOCUMENTS

| | | | | |
|---|---|---|---|---|
| EP | 1535531 A1 * | 6/2005 | ............ | A45D 20/06 |
| KR | 100665242 B1 * | 1/2007 | ............ | A45D 20/06 |

* cited by examiner

*Primary Examiner* — Stephen M Gravini
(74) *Attorney, Agent, or Firm* — Knobbe, Martens, Olson & Bear LLP (57) ABSTRACT

Systems, devices, and methods for drying wefted hair. Systems can include an enclosure for drying wefted hair by removing moisture from the wefted hair. The wefted hair can be hung on racks having a plurality of tines. The wefted hair can be placed on trays.

20 Claims, 11 Drawing Sheets

WEFTED HAIR DRYER

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57 and should be considered a part of this specification.

BACKGROUND

Field

The present disclosure relates generally to an enclosure for drying hair. More particularly, the present disclosure relates to devices, systems, and methods for drying wefted hair by removing the moisture from the wefted hair.

Description of the Related Art

Hairstylist usually have the need to dry wefted hair but not the time to hold a hand held dryer to do so. Hairstylists can place the hair in a hooded dryer; however, the moisture from the wefted hair can drip down into the dryer and short the dryer out. As well, existing hooded dryers do not provide for airflow, which can further cause the dryer to short circuit. As well, existing dryers will frequently not dry the wefted hair evenly.

SUMMARY

The devices, systems, and methods disclosed herein have several features, no single one of which is solely responsible for its desirable attributes. Without limiting the scope as expressed by the claims that follow, its more prominent features will now be discussed briefly. After considering this discussion, and particularly after reading the section entitled "Detailed Description" one will understand how the features of the system and methods provide several advantages over traditional systems and methods.

In accordance with one aspect, a system for drying wefted hair is provided. The system comprises an enclosure configured to allow the flow of air and moisture through the enclosure, a rack having a plurality of tines positioned within the enclosure, a heating element configured to heat air that flows into the enclosure, an ion generator configured to supply negative ions into the enclosure, a fan configured to direct said heated air through the enclosure; and a controller configured to control an operational setting of one or more of the heating element, the ion generator, and the fan. The wefted hair can be hung from the tines of the rack in the enclosure, and one or both of the fan and the heating element are operable to heat the air in the enclosure to remove moisture from the wefted hair to dry the wefted hair.

BRIEF DESCRIPTION OF THE DRAWINGS

The disclosed aspects will hereinafter be described in conjunction with the appended drawings, provided to illustrate and not to limit the disclosed aspects, wherein like designations denote like elements. The drawings disclose illustrative embodiments. They do not set forth all embodiments. Other embodiments may be used in addition to or instead. Conversely, some embodiments may be practiced without all of the details that are disclosed. It is to be noted that the figures provided herein are not drawn to any particular proportion or scale, and that many variations can be made to the illustrated embodiments.

DETAILED DESCRIPTION OF THE INVENTION

As used herein, the term "wefted hair" can refer to any hair that is attached to a weft, such as a wefted hair extension. Wefted hair is hair attached to a weft or track. Wefted hair, preferably, can be a smaller section of hair that does not cover the head. Wefted hair can be used for temporary hair extensions, which can be used to add length, fullness, and/or color to human hair. The hair used to make the wefted hair can be human, artificial, and/or synthetic hair. The hair can be permed, dyed, and/or flat ironed.

Disclosed is a stand-alone dryer that can sit off to the side or in a back room at a salon, theater, home, or the like. The dryer can optionally be in cabinet form. The dryer can optionally be portable. The dryer can optionally be permanently installed. As well, the dryer can remove the moisture from the wefted hair. This can prevent the hair from dripping down into the dryer and shorting the dryer out. As well, this dryer can assist the hairstylist by freeing up other dryers for client use for other services. Additionally, this dryer can assist in theaters or the like, where there is a need to wash and dry numerous wefted hairs after performances and therefore require a quicker and more convenient method of getting them dry for the next show. This dryer is temperature controlled to inhibit damage (e.g., heat damage) to the wefted hair, and the wefted hair can be dried with minimum handling.

Wefted hair made with human hair requires special care and maintenance to prevent damage to the hair and keep the wefted hair in optimum condition. Preferably, drying the wefted hair involves delicate and minimum handling. Drying wefted hair at the salon can involve the process of shampooing, combing out, and then drying 8 to 12 ounces of extension hair, which can be a very long and tedious job. The wefted hair can be gently patted with a towel to remove some of the excess moisture before being placed in the dryer. The wefts (the tracks that the hair is attached to) can take a long time to dry. The wefted hair can be susceptible to mildew or microbial growth if it remains wet or takes too long to dry.

Advantageously, the dryer can dry the wefted hair to a desired dryness level in about 10 to about 15 minutes. In some embodiments, the wefted hair can be dried in less than 10 minutes. In some embodiments, the wefted hair can be dried in more than 15 minutes. In some embodiments, the drying time for the wefted hair can be between 5 minutes and 60 minutes. The drying time can depend on the thickness, type, amount, and/or length of the hair used, and/or the weft used.

Figure 1A:
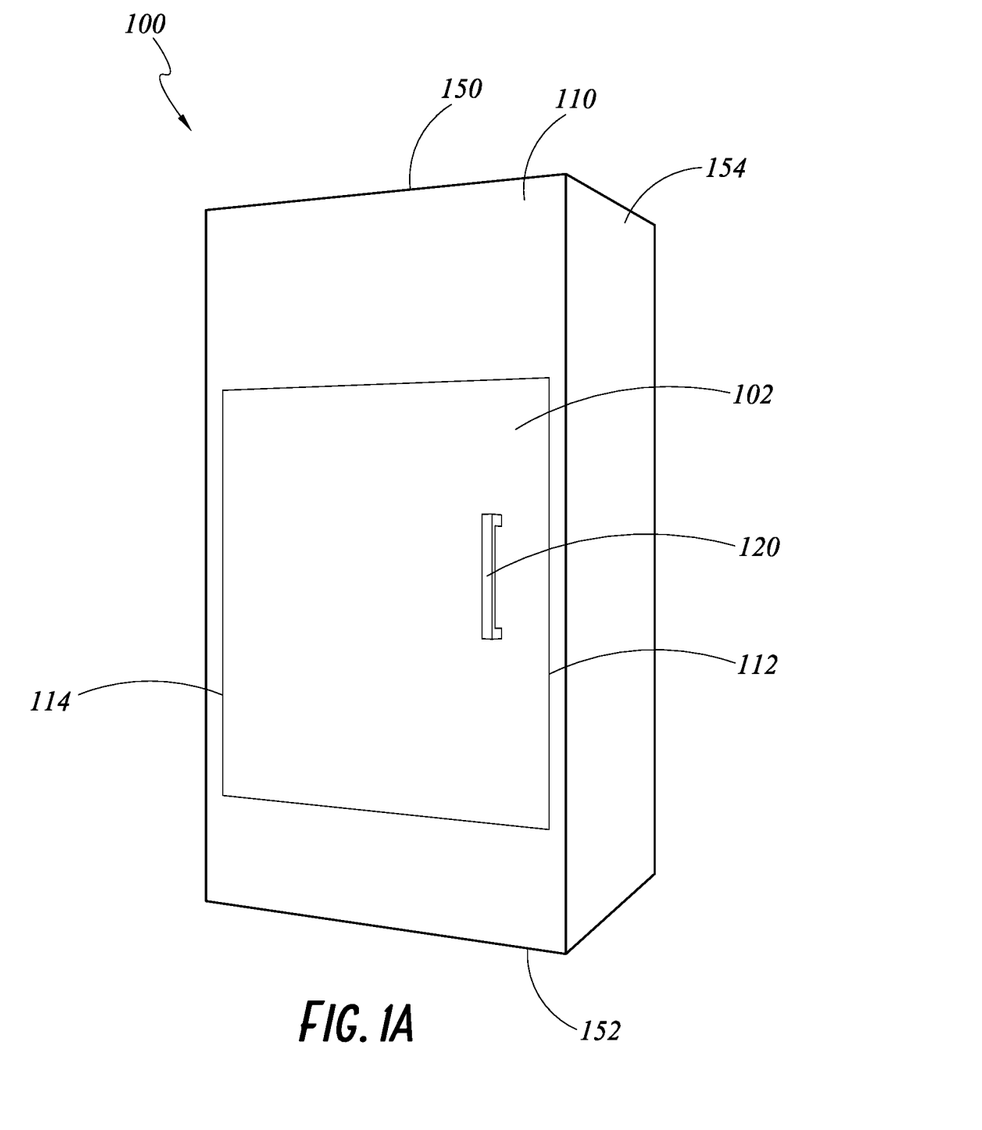
FIG. 1A is a perspective view of an embodiment of a dryer with the door closed.
Figure 1B:
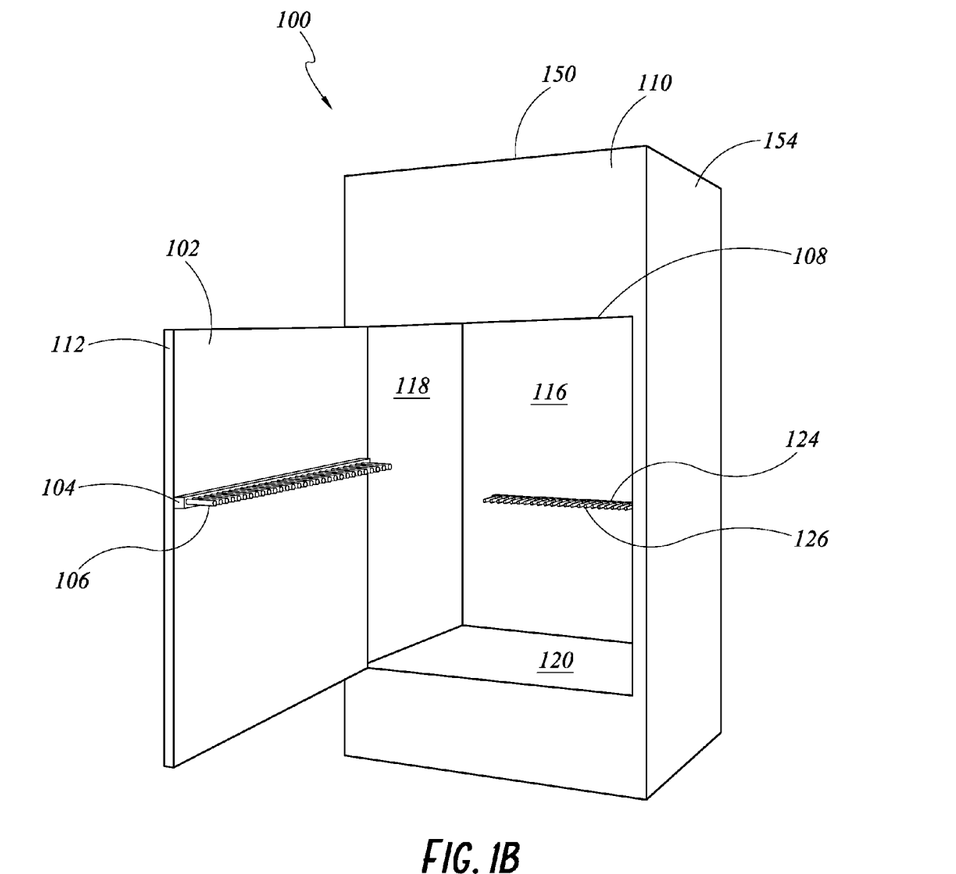
FIG. 1B is a perspective view of the dryer shown in FIG. 1A with the door open, showing the racks with a plurality of tines for hanging wefted hair.

FIGS. 1A and 1B depict one embodiment of a dryer (also referred to as an enclosure) 100. The dryer 100 may define an internal volume, and be operable to specifically retain heat in the internal volume of the dryer 100. The dryer 100 may include a variety of shapes and sizes, and may be made from a variety of materials and/or components. In some embodiments, for example, the dryer 100 may be made of metal, wood, glass, a synthetic material, a natural material, a composite, and/or any other desired material. In the embodiment depicted in FIGS. 1A and 1B, the dryer may have a shape of a rectangular prism and/or a cube.

The illustrated dryer (also called enclosure) in FIGS. 1A and 1B has a top 150, a bottom 152, and at least one sidewall that extends generally between the top 150 and the bottom 152. In the illustrated configuration, the dryer 100 has a front wall 110, an opposing rear wall 142, and sidewalls 154. The internal junctures of two or more walls can be radiused to reduce the occurrence of tight corners. In the illustrated configuration, the dryer 100 has a generally rectangular shape. In some configurations, the dryer 100 can have a generally spherical, cylindrical, or other suitable shape.

The dryer can have any suitable shape, size, and configuration for use in a hairstyling salon, theater, home, or the like. In some configurations, the shape and sizing of the dryer is less important than the internal volume of the dryer. In some embodiments, the internal volume of the enclosure can be between about 300 to 1300 liters. For example, in some configurations, the dryer is designed to retain a certain amount of wefted hair. The height (from top 150 to bottom 152) of the dryer 100 can be between about 20 inches and about 40 inches. In one embodiment, the dryer 100 can have a height of about 30 inches. The width (from side to side) of the dryer can be between about 10 inches and about 20 inches. In one embodiment, the dryer can be about 17 inches wide (from side to side). The depth (from front 110 to back 142) can be between about 10 inches and about 20 inches. In one embodiment, the dryer can be about 15 inches deep (from front to back).

Figure 2:
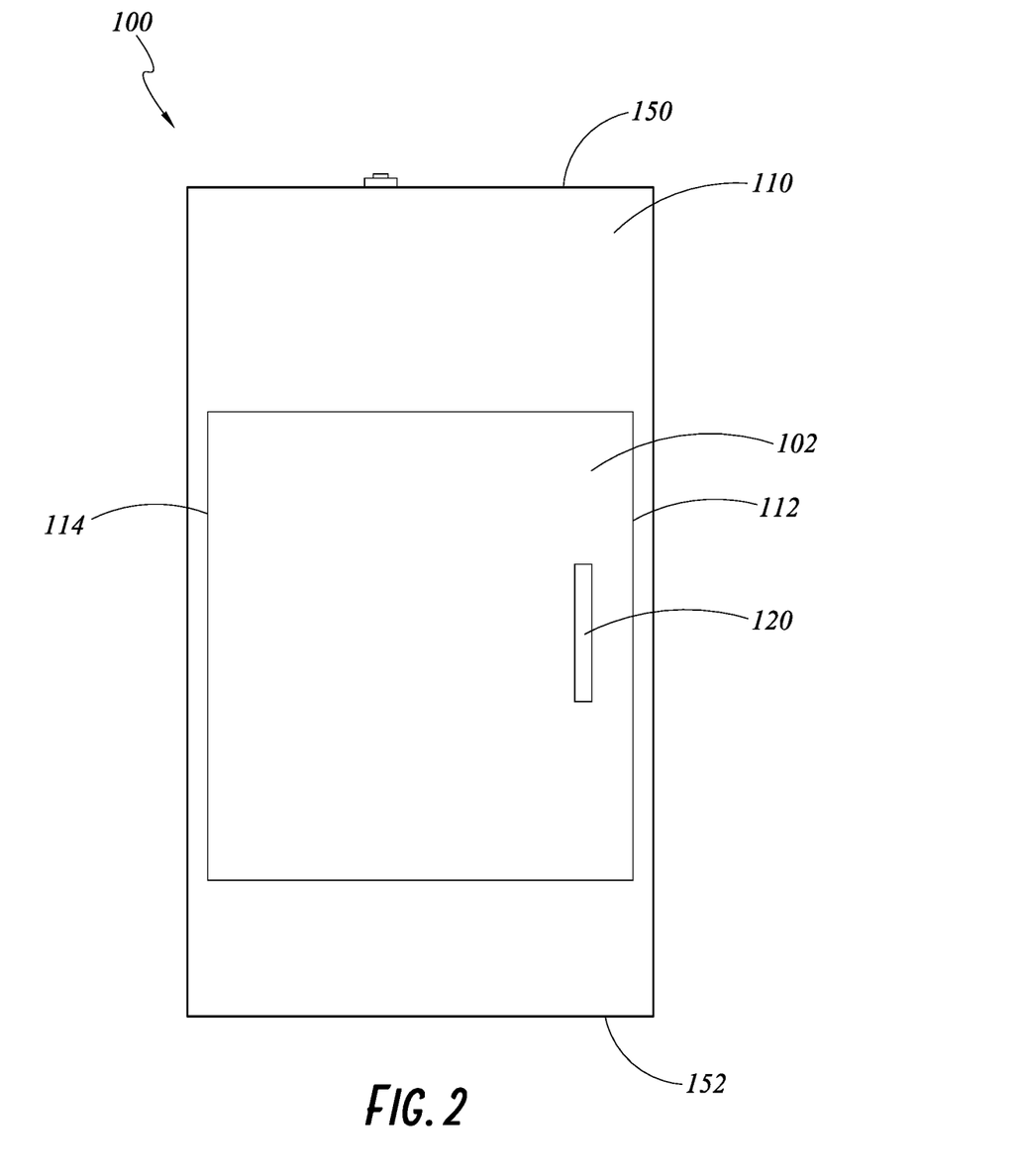
FIG. 2 is a front view of the dryer of FIG. 1A with the door closed.

The enclosure 100 can allow the flow of air and moisture through the enclosure. As illustrated in FIGS. 1A and 1B, the enclosure 100 can have a door 102 that is moveable between open and closed positions relative to an opening 108 of the enclosure 100. FIGS. 1A and 2 show an embodiment of the enclosure 100 with the door 102 in the closed position. When the door 102 is in the closed position, the interior volume of the enclosure 100 is inaccessible. FIG. 1B shows the embodiment of the enclosure 100 with the door 102 in an open position. When the door 102 is in an open position, the inner volume of the enclosure is accessible. The door 102 can have a first end 112 and a second end 114. In some embodiments, the second end 114 is dynamically connected with another component of the enclosure 100. The second end 114 can be connected to one or more walls of the enclosure 100 (e.g., front, rear, left, right, top, and/or bottom) via one or more hinges. In the illustrated configuration, the door 102 is hingably connected to the front wall 110. This hinged connection allows the door 102 to be moved between a first (open) position, and a second (closed) position.

The door 102 can further have a handle 120. The handle 120 can assist in opening and closing the door 102. In some embodiments, the door 102 can further have a lock to secure the door 102 in the closed position. In some embodiments, the door 102 can be made from the same or substantially similar material as the walls of the enclosure 100. In some embodiments, the door 102 can be transparent, such that a user can see through the door. In some embodiments, the door 102 can be made from glass.

In some configurations, the door 102 can be a sliding door or other suitable closing mechanism. The door 102 can be attached to any surface of the enclosure (e.g., front, left, right, rear, bottom, and/or top). Preferably, the door is attached to the front wall of the enclosure. In some embodiments, the door 102 may be slidably connected to the front side 110 by a track or similar device. This allows for the door 102 to slide between an open position and a closed position within the plane that defines the opening 108 of the enclosure 100. Although this embodiment is not specifically depicted, a person of skill in the art would understand, using the present disclosure as a guide, how to provide a sliding door on an enclosure described herein.

Figure 3:
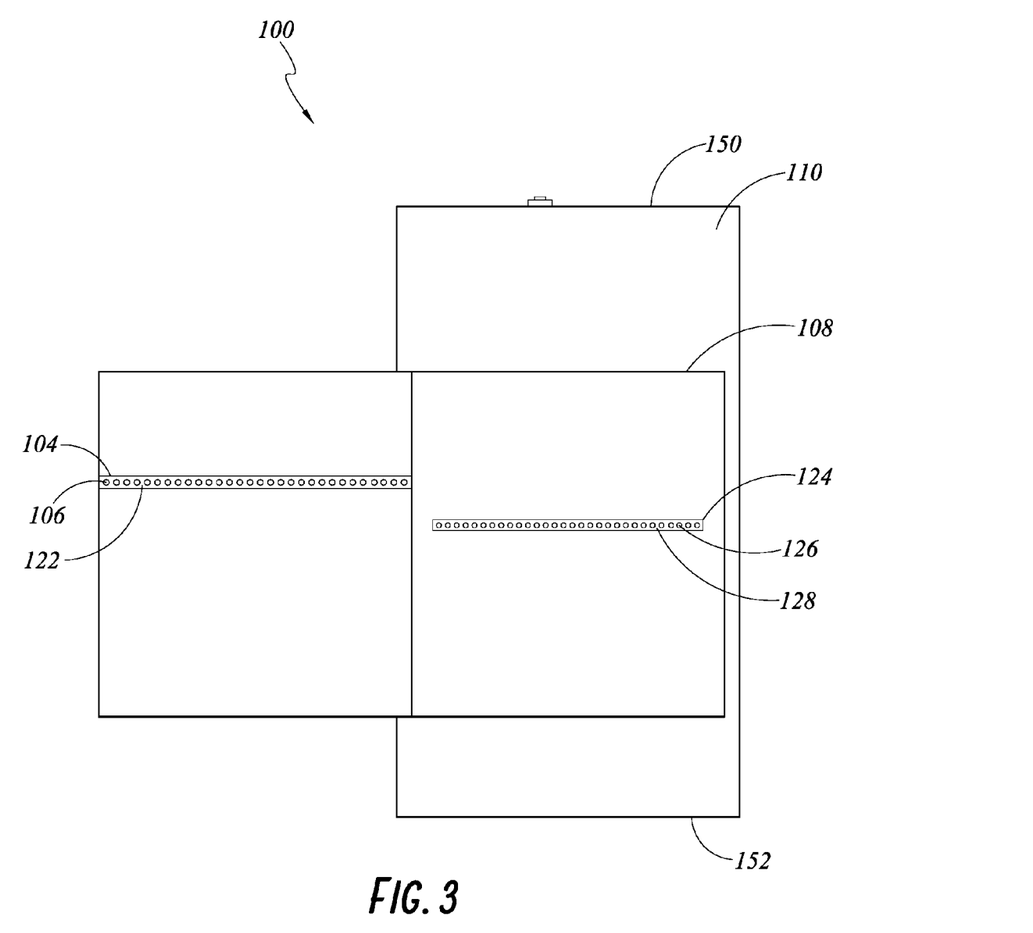
FIG. 3 is a front view of the dryer of FIG. 1A with the door open, showing racks with a plurality of tines for hanging wefted hair.
Figure 4:
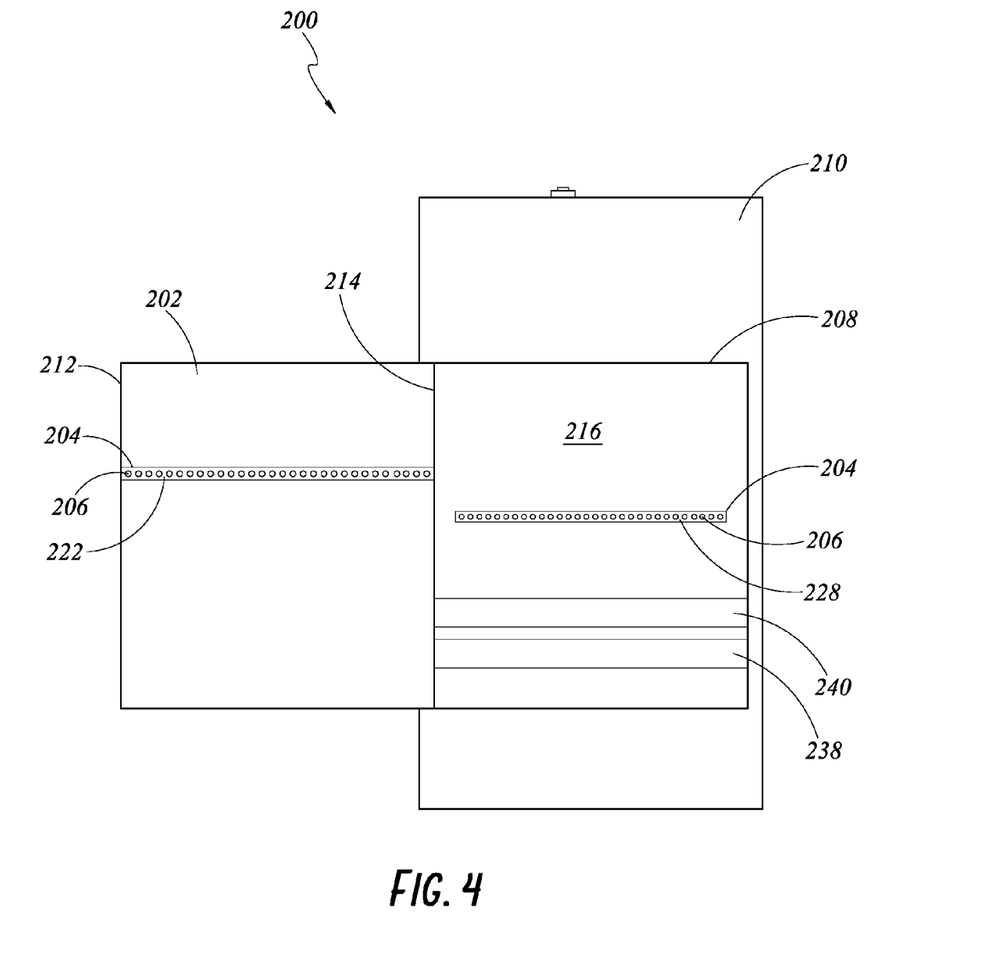
FIG. 4 is a front view of another embodiment of a dryer with the door open, showing racks with a plurality of tines for hanging wefted hair and trays for holding wefted hair.

The opening 108 can have any suitable size and configuration that allows the user to place wefted hair in the enclosure. In the illustrated embodiment in FIG. 1B, the opening 108 is generally rectangular. In some embodiments, the opening 108 can be generally circular, elliptical, asymmetrical, or the like. The opening 108 allows the user to access the interior of the enclosure 100, such as accessing the racks 104, 124 and/or trays 238, 240 as illustrated in FIGS. 3 and 4. Preferably, the opening 108 is in the front surface, but the opening can be in the top, side, and/or rear surface.

The enclosure 100 has an internal volume, which can have interior surfaces or walls. The enclosure 100 can have an interior left sidewall 118, interior right side wall, interior back wall 116, interior top, and interior bottom 120. The sidewalls and back wall can extend generally between the interior bottom 120 and interior top.

In some embodiments as illustrated in FIGS. 3 and 4, there can be one or more racks having a plurality of tines positioned within the enclosure. The wefted hair can hang from a rack or racks inside the enclosure. As illustrated in FIG. 3, in some embodiments, there can be a rack 104 positioned on the inside of the door 102. As illustrated in FIG. 3, in some embodiments, there can be a rack 104 attached to the inside of the door 102. The rack 104 can be attached to the door 102 by any suitable attachment mechanism, such as, glue, fasteners (e.g., bolts, screws), clips, an over the door hanger, or the like. The rack 104 can extend from the first end 112 to the second end 114 of the door 102. The rack 104 can extend at least partially from the first end 112 to the second end 114 of the door 102. In some embodiments, the rack 104 can have a continuous piece. In some embodiments, the rack 104 can have discrete pieces. In some embodiments, the rack 104 can have a length that is between about 2 inches and 36 inches. In some embodiments, the rack 104 can have a length that is between about 6 inches and 36 inches. In some embodiments, the rack 104 can be up to 16 inches long. In other examples, the rack can be longer to shorter, such as 6, 8, 10, 12, 15, 17, 18, 20, 22, 24 or 36 inches long.

In some embodiments, there can be one or more racks 104 on the door 102. In some embodiments, there can be no racks 104 on the door 102. In some embodiments, there can be between 1 and 20 racks on the door 102. In some embodiments, there can be between 2 and 5 racks on the door. In some embodiments, there can be 4 racks on the door.

As illustrated in FIG. 3, in some embodiments, there can be a rack 124 positioned in the interior of the enclosure 100. The rack 124 can be positioned on an interior surface (e.g., side, back, top, and/or bottom). The rack 124 can be attached to an interior wall by any suitable attachment mechanism, such as glue, adhesive, fasteners, or the like. The rack 124 can be free standing, for example, suspended from an interior top or bottom surface. As illustrated in FIG. 3, the rack 124 can be attached to an interior back surface 116. The rack 124 can extend at least partially from left to right sides of the interior back surface 116. In some embodiments, the rack 124 can extend across the entire interior back surface 116. In some embodiments, the rack 124 can be a continuous piece. In some embodiments, the rack 124 can be discrete pieces. In some embodiments, the rack 124 can have a length that is between about 2 inches and 36 inches. In some embodiments, the rack 124 can have a length that is between about 6 inches and 36 inches. The rack 124 can be up to 16 inches long. In other examples, the rack 124 can be longer to shorter, such as 6, 8, 10, 12, 15, 17, 18, 20, 22, 24 or 36 inches long.

In some embodiments, there can be one or more racks 124 positioned on one or more interior walls of the enclosure 100. In some embodiments, there can be no racks 124 positioned on an interior wall of the enclosure 100. In some embodiments, there can be between 1 and 20 racks on one or more interior walls of the enclosure 100. In some embodiments, there can be between 2 and 5 racks on an interior wall of the enclosure. In some embodiments, there can be 5 racks on a side interior wall of the enclosure. In some embodiments, there can be 3 racks on a back interior wall of the enclosure.

In some embodiments, as illustrated in FIG. 1B, the rack 104, 124 can have a generally rectangular shape. In some embodiments, the rack 104, 124 can have a generally cylindrical, triangular, asymmetrical, or the like shape. In some embodiments, as illustrated in FIGS. 1B and 3, the rack 104, 124 can extend generally parallel to the horizontal. In some embodiments, the rack 104, 124 can extend generally parallel to vertical. In some embodiments, the rack 104, 124 can extend at an angle from the horizontal.

The rack 104, 124 can have a plurality of tines 106, 126. The tines 106, 126 are can hold part of the wefted hair such that the wefted hair can hang inside the enclosure. Having the wefted hair hang helps the hair and weft dry evenly. A wefted hair can be draped over one or more tines 106, 126. In some embodiments, the rack 104, 124 can have between 1 and 50 tines. The number of tines 106, 126 can depend on how much wefted hair the user wants to hang in the dryer. In some embodiments, a 17-inch rack can include 42 individual tines that are separated by a 0.25 inch gap between adjacent tines.

The tines 106, 126 in some embodiments can be similar in size to the tines of a comb. The tines can have any number of different shapes. For example, towards the upper end of sizes, the tines can be 0.5 inches apart and 0.12 inches in diameter and still hold the wefted hair properly. In some embodiments, as illustrated in FIGS. 1B and 3, the tines 106, 126 are generally cylindrical in shape. In some embodiments, the tines 106, 126 can have a diameter between about 0.06 inches and 0.12 inches. The tines can have a round cross-section and have a diameter of between 0.06 and 0.12 in. In some embodiments, the tines 106, 126 can be generally rectangular, triangular, asymmetrical or the like. In some embodiments, the tines 106, 126 can have a uniform diameter. In some embodiments, the tines 106, 126 can have a varying diameter, for example, the cross-sectional area of the tine may decrease when going from the end of the tine attached to the rack to the exposed free end, such that the exposed end of the tine is thinner than the end attached to the rack. In some embodiments, the tine can have a hook (e.g., curved, angular, or the like) shape at the exposed end of the tine.

In some embodiments, the space 122, 128 between tines 106, 126 can be uniform. In some embodiments, the space 122, 128 between tines 106, 126 can be varied. In some embodiments, a space 122, 128 between the tines 106, 126 is between about 0.1 inches and about 1 inch wide. Preferably, the tines are spaced between 0.1 and 0.5 inches apart. In some embodiments, a space 122, 128 between the tines 106, 126 is about 0.25 inches. In some embodiments, the tines 106, 126 are spaced between about 0.30 inches and about 0.4 inches center to center.

In some embodiments, the tines 106, 126 can be attached to the enclosure 100 without the use of a rack 104, 124. The tines 106, 126 can be attached to the enclosure 100 with any suitable attaching mechanism, such as, glue, adhesive, fasteners, clips, or the like. The tines 106, 126 can be attached to the racks 104, 124 with any suitable attaching mechanism, such as, glue, adhesive, fasteners, clips, or the like.

The rack(s) 104, 124 can be adjustable, such that the position of the rack(s) 104, 124 in the interior of the enclosure can be changed. In some embodiments, the positions of the tines 106, 126 can be adjustable, such that the position of the tines 106, 126 can be changed. For example, the tines 106, 126 can be moved (e.g. slid) closer together or farther apart. The tines 106, 126 can be arranged in a line, curve, zigzag, circle, or other suitable arrangement.

The position of the rack 104, 124 can be adjusted to accommodate the length of the wefted hair being hung on it, for example, a rack 104, 124 can be moved closer to the top of the enclosure 100 when hanging a longer wefted hair extension. Wefted hair can be between about 2 inches and about 40 inches in length. There can be one or more racks in the dryer. The position of the rack 104, 124 can be adjusted to accommodate other racks. The wefted hair can touch one or more racks. For example, when hanging from a top rack, the wefted hair may touch lower racks or tines on lower racks.

In some configurations, one or more racks can be attached to the door of the dryer. In some configurations, there can be no racks attached to the door of the dryer. In some configurations, at least one rack can be attached to an interior wall of the dryer (e.g. front, left, right, and/or back wall). In some configurations, at least one rack can be attached to the door of the dryer and at least one rack can be attached to an interior wall of the dryer. Preferably, the rack is attached to a sidewall and/or the back wall of the dryer.

In some configurations, as illustrated in FIG. 4, the enclosure 200 can further have one or more trays 238, 240 removably positionable within the enclosure 200. The tray(s) 238, 240 can hold wefted hair. Wefted hair that has been processed can be placed in the tray(s) 238, 240. Coloring, permanent waves, and other chemical processes done to hair can require heat as part of the processing. Because of the processing, it may be preferred that the wefted hair is laid on a tray 238, 240 as opposed to hung from a rack 204, 224 with a plurality of tines 206, 226. For example, wefted hair can be wrapped in a processing plastic cap and placed on a tray 238, 240 to be processed.

The tray(s) 238, 240 can have any size and shape suitable for holding wefted hair, more specifically processed wefted hair. The tray can have a basket shape. The tray can be a shelf. The tray(s) 238, 240 can be retractable, such that they can slide in and out of the enclosure 200. The tray(s) 238, 240 can be removably positionable, such that the entire tray can be taken out of the enclosure 200 (e.g., when there is no processed hair to place in the enclosure 200). The tray(s) 238, 240 can be adjustable, such that the position of the tray in the enclosure 200 can be changed. The tray can be permanently positioned.

In some configurations, the tray(s) 238, 240 can attach to or rest on at least one interior wall or surface of the enclosure 200 (e.g., interior left side 218, interior right side, bottom 220, and/or top). In some configurations, the tray(s) 238, 240 can attach to or rest on shelves (not shown) inside the enclosure 200. In some configurations, the tray(s) 238, 240 can extend partially along the back interior surface 228. In some configurations, the tray(s) 238, 240 can extend generally between an interior left side wall 218 and an opposite interior right side wall. In some configurations, the tray(s) 238, 240 can attach to or hang from the door 202.

In the illustrated configuration in FIG. 4, the trays 238, 240 are positioned below the racks 204, 224. In some configurations, the trays 238, 240 can positioned below, at the same level as, and/or above the racks 204, 224, or a combination of those positions. The trays 238, 240 can be removable. In some configurations, the dryer can have one or more trays. In some configurations, the dryer has no trays.

Figure 7:
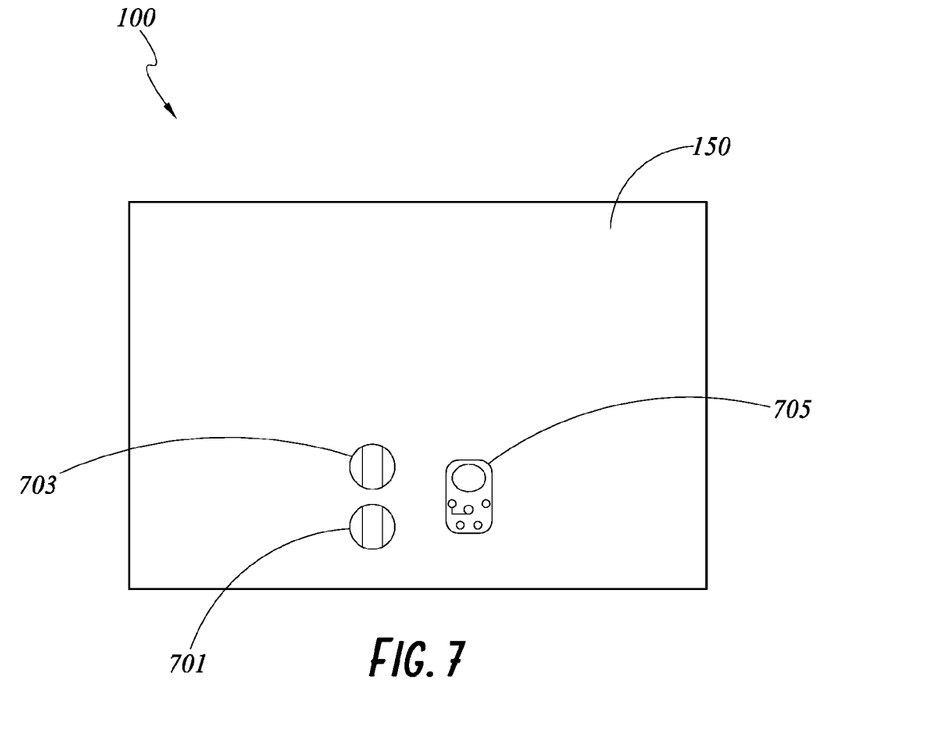
FIG. 7 is a top view of the dryer of FIG. 1A, showing a configuration of the controls for the dryer.
Figure 7A:
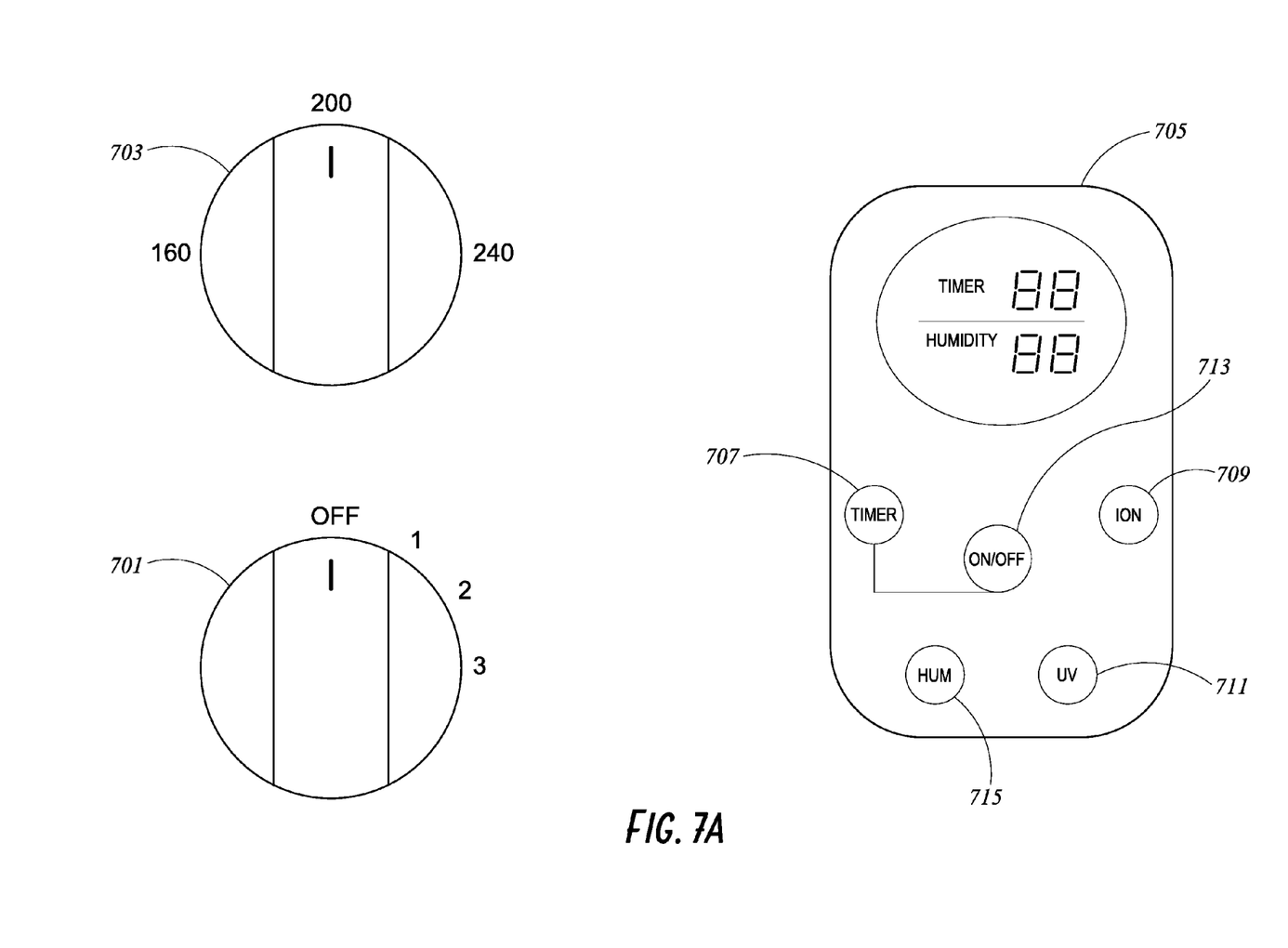
FIG. 7A is an enlarged view of the configuration of controls shown in FIG. 7.
Figure 8:
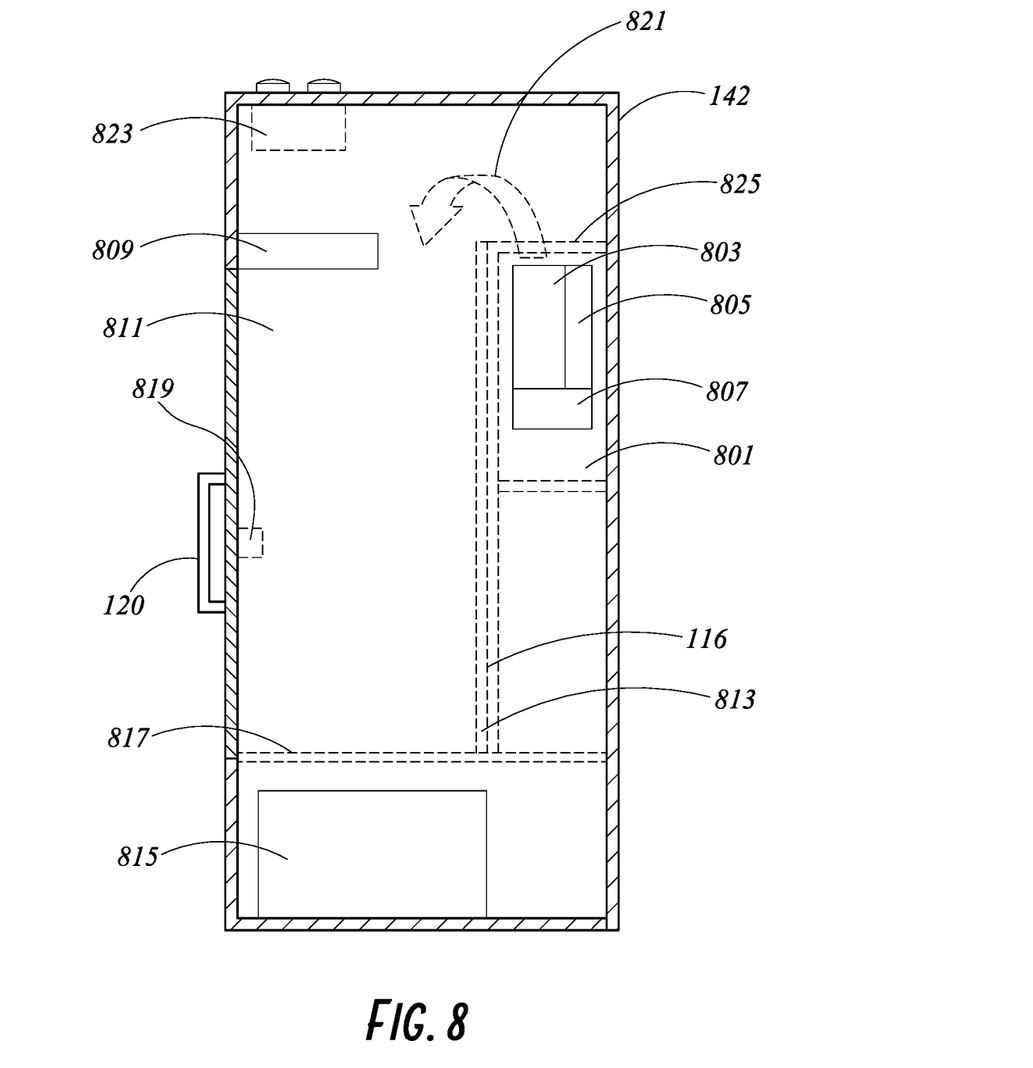
FIG. 8 is a cross-sectional side view of the dryer of FIG. 1A.
Figure 9:
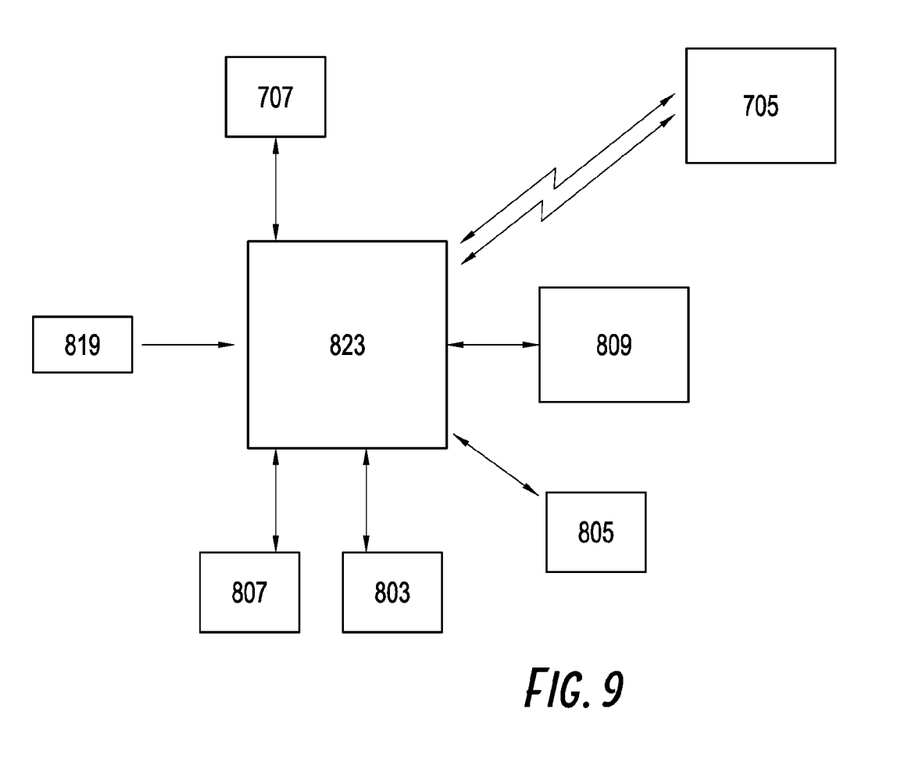
FIG. 9 is a schematic block diagram showing an embodiment of a control unit of the dryer of FIG. 1A.

The enclosure 100 can have a heating element 803 that heats the air that flows through the enclosure 100, as illustrated in FIG. 8. In some embodiments, the heating element 803 can provide about 600 W. In some embodiments, the operation of the heating element 803 can controlled by and in communication with a controller 823. In some configurations, the heating element 803 can be controlled by a thermostat. The thermostat can provide for a maximum temperature of about 200° F. in some embodiments, though other maximum temperatures can be provided. The preferred temperature for drying wefted hair is about 200° F. In some configurations, the heating element 803 can provide a temperature up to about 240° F. The dryer 100 can have one or more sensors 819, as illustrated in FIGS. 8 and 9, (e.g., temperature sensors) that communicate sensed information to the controller 823 (e.g., communicate sensed temperature of the interior volume of the enclosure 100), and the controller 823 can operate the heating element 803 so that the temperature is maintained at approximately a selected temperature set point. In some embodiments, the one or more sensors 819 can be positioned inside the dryer 100, 200. In some embodiments, the one or more sensors 819 can be positioned inside the interior area/volume 811 (e.g., interior volume of the dryer 100, 200). In one embodiment, the temperature set point is user selected, as discussed further below. In some configurations, the controller 823 can turn the heating element 803 on or off, regulating the flow of a heat transfer fluid, as needed, to maintain the selected temperature, as illustrated in FIG. 7A with button 713. In some configurations, the heating element 803 can provide varying levels of heat. As illustrated in FIG. 7A, the dial 703 can provide a selected temperature for the enclosure. In some embodiments, the dial 703 can control the level of heat the heating element 803 provides (e.g., via a controller 823, as discussed above).

The enclosure 100 can have an ion generator 805 that supplies negative ions into the enclosure 100, as illustrated in FIG. 8. In operation, the ion generator 805 can change the ions in the air to negative ions, which can aid in providing the desired texture of the hair. A controller 823 can control the operation of and be in communication with the ion generator 805. The operation of the ion generator 805 can be controlled by a switch, such that the ion generator can be turned on and off, as illustrated in FIG. 7A with button 709. The ion generator 805 can include one or more 30-diode ion generator boards to supply negative ions to help dry the wefted hair while avoiding overly drying the wefted hair. In some embodiments, the ion generator can include two 30-diode ion generator boards. The two 30-diode ion generator boards can be driven by a low noise high volume fan that can be controlled by the operator.

The enclosure 100 can have a fan 807 that directs the heated air and/or ions through the enclosure 100, as illustrated in FIG. 8. The heating element 803 and/or fan 807 are operable to heat the air in the enclosure 100 to remove moisture from the wefted hair and to dry the wefted hair to a desired dryness level. Ideally, the fan 807 is low noise because it will be used around people. The dryer 100 is designed for use in hair salons and/or homes and it would be preferable if people could easily converse while the fan is being used. However, in some configurations, the dryer 100 could be stored in a back room or the like, where the noise of the fan 807 would not be noticeable and the fan 807 would not need to be low noise. In some embodiments, the fan 807 can be controlled by a switch, such that the fan 807 can be turned on and off. Preferably, the fan 807 has adjustable speeds. For example, the fan 807 can have one or more levels. In some embodiments, the fan 807 can be a three phase fan. As illustrated in FIG. 7A, the dial 701 can control the speed or level of the fan 807. In some configurations, the fan 807 can be controlled by and in communication with a controller 823.

In some configurations, the enclosure 100 can have a germicidal light source 809 that can possibly sterilize the wefted hair and possibly kill lice and any of their eggs that may infect the wefted hair, along with bacteria, mold, viruses, and/or other microorganisms that may be present in the wefted hair, as illustrated in FIG. 8. A germicidal light source 809, such as a shortwave ultraviolet (UV) light, can be used to help sterilize the wefted hair. The enclosure 100 can further have an ultraviolet light source that can direct ultraviolet light within the enclosure to sterilize the wefted hair. As used herein "sterilize" is to at least partially make something free from bacteria or other living microorganism, there does not need to be a complete removal of bacteria. The UV light source 809 can provide light between about 100 nm and about 280 nm. The UV light 809 can provide light between about 230 nm and about 280 nm. The UV light 809 can provide light about 254 nm. The UV light source 809 can be a UVC (germicidal) light bulb. The UV light source 809 can also be used to sterilize the interior surfaces, racks, trays, and/or other components in the enclosure. In some configurations, the UV light source 809 can be positioned in the interior area 811 (e.g., interior volume of the dryer 100, 200), such that the UV light source 809 bathes the wefted hair in UV light in order to further sterilize the pieces of wefted hair. In some embodiments, the position of the UV light source 809 is adjustable. In some embodiments, the position of the UV light source 809 is permanent. In some embodiments, the UV light source 809 can be any suitable size or configuration to bathe the wefted hair with UV light. In some embodiments, the UV light source 809 can be suspended from an interior top surface or bottom surface 120. In some embodiments, the UV light source 809 can be attached by any suitable attaching mechanism to an interior wall (e.g., left 118, right, back 116, front, and/or door 102).

In some configurations, the operation of the UV light source 809 can be controlled by and in communication with a controller 823. The operation of the UV light source 809 can be controlled by a switch, such that the UV light 809 can be turned on and off, as illustrated in FIG. 7A with button 711. In some embodiments, the UV light source 809 can provide adjustable levels of light.

In some configurations, the dryer 100 can have one or more sensors 819 to detect a parameter in the enclosure 100 and to communicate it to the controller 823 (e.g., to adjust the operation of the heating element 803, ion generator 805 and/or fan 807). In one embodiment, the one or more sensors 819 can include at least one temperature sensor. In one embodiment, the one or more sensors 819 can include at least one humidity sensor to detect the humidity level inside the enclosure 100, as illustrated in FIG. 8. The humidity sensor can be controlled by a switch, such that the humidity sensor can be turned on and off, as illustrated in FIG. 7A with button 715. The operation of the humidity sensor 819 can be controlled by and in communication with a controller 823. The temperature and/or humidity level in the enclosure 100, 200 can be displayed as part of the controls, as illustrated in FIG. 7A with display 705. The temperature and/or humidity level can be displayed as a number or can be displayed as whether it is in or out of a predetermined range. The humidity sensor 819 can measure relative humidity. The humidity sensor 819 can sense the relative humidity. The humidity sensor 819 can act like a switch, such that the controller 823 would automatically turn off or on the heating element 803 and/or fan 807 based on a selected humidity level. For example, the temperature and/or humidity sensor 819 could continuously (or intermittently) communicate sensed temperature and/or humidity levels in the enclosure 100, 200 to the controller 823, and the controller 823 could compare the sensed temperature and/or humidity level to a predetermined temperature and/or humidity set point indicative of the drying process being complete. Once the controller 823 determined the sensed temperature and/or humidity level communicated to it by the temperature and/or humidity sensor 819 was equal to or less than the predetermined temperature and/or humidity set point, the controller 823 could discontinue power to the heating element 803 and/or fan 807.

Optionally, the dryer 100, 200 can have a timer that can automatically shut the unit off (e.g., discontinue power to the heating element 803 and/or fan 807) when a selected time is reached. In some configurations, the dryer 100 can have a timer 707, as illustrated in FIG. 7A. In some configurations, the timer 707 can be electrically connected to one or both of the fan 807 and the heating element 803, the timer 707 operable to automatically turn the system off when a preselected time has been reached. The timer 707 can control the heating element 803 and/or the fan 807. The timer 707 can automatically shut-off the heating element 803 and/or fan 807 after a selected time, for example, 1, 2, 4, 10, 15, 20, or 30 minutes. The remaining time can be displayed in the display 705, as illustrated in FIG. 7A. The timer can be controlled by and in communication with a controller 823. In one embodiment, the dryer 100, 200 can provide a visual or aural indication once the drying process was completed. For example, once the time set by the timer expired, the dryer 100, 200 can optionally emit a sound (e.g., alarm) to indicate to the user that the drying process has been completed.

The dryer 100 can have a controller 823 that can control an operational setting of at least one of the heating element 803, ion generator 805, fan 807, UV light source 809, timer 707, and/or at least one temperature or humidity sensor 819.

In some examples, any of the following components can provide and/or control the power to the dryer system: the heating element, the thermostat, the ion generator, the fan, or the dials located on the top 150 of the enclosure 100. FIGS. 7 and 7A show examples of the dials 701, 703 located on the exterior of the enclosure 100. In some embodiments, there can be physical dials and/or controls. In some embodiments, there can be digital dials and/or controls, such as a touch screen or interactive display.

Additionally, the dryer 100, 200 contains all electrical components away from any moisture source (e.g., moisture being removed from the wefted hair) to inhibit short circuiting of the electrical components. In some configurations, one or more of the heating element 803, fan 807, and/or ion generator 805 can be disposed away from the racks 104, 124 to inhibit contact with moisture that is removed from the wefted hair. In some configurations, one or more of the heating element 803, fan 807, and/or ion generator 805 can be disposed in a compartment within the enclosure 100. As illustrated in FIG. 8, the enclosure 100 can have an interior compartment 801 that separates the heating element 803, fan 807, and/or ion generator 805 from the rack(s) and/or tray(s). The interior compartment 801 can have one or more walls that separate the heating element 803, fan 807, and/or ion generator 805 from the main area/volume 811 where the wefted hair is placed. There needs to be a passage so that heated air can pass from the interior compartment 801 to the main area 811. The passage can be any suitable size or shape and positioned in any suitable location. In some configurations, the heated air blows across the hair extensions to aid in drying the hair and weft evenly. The arrow 821 in FIG. 8 shows a possible direction of air flow from the compartment 801 into the main area/volume 811. In some embodiments, there can be one or more openings or passages 825, as illustrated in FIG. 8, at or near the top of the interior compartment 801 to allow heated air and/or ions to flow out of the top of the interior compartment 801 and into the main area/volume 811 that contains wefted hair to be dried. In some embodiments, the one or more openings or passages 825 can be at or near the bottom and/or the side(s) of the interior compartment 801.

Figure 5:
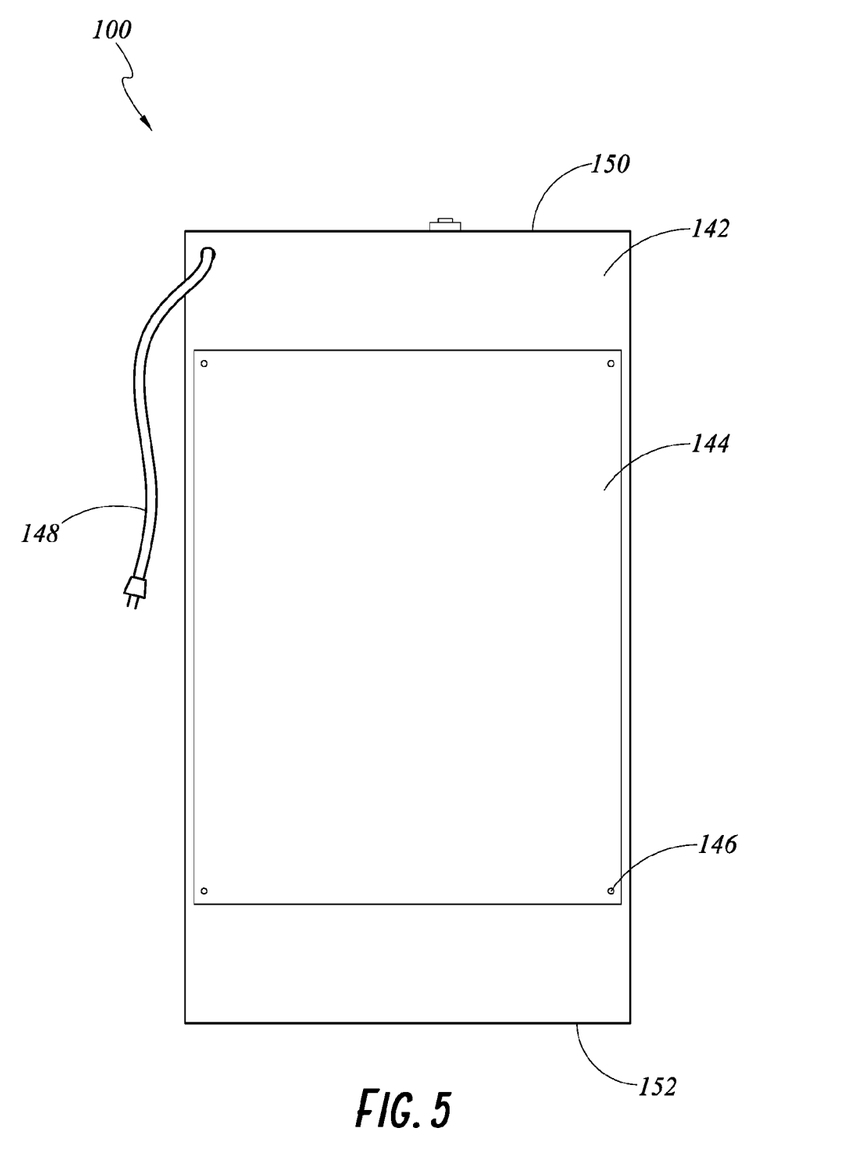
FIG. 5 is a rear view of the dryer of FIG. 1A.

There can be a removable access panel 144 on one or more of the walls of the enclosure 100 so that a user can access the interior compartment 801. As illustrated in FIG. 5, the access panel 144 can be on the back wall 142. The access panel 144 can be secured with a plurality of fasteners 146, such as bolts, screws, or the like. The access panel 144 can be a door, which can be opened to enable access to the components in the interior compartment. The access panel 144 can be secured, such as with a lock or latch. The access panel 144 can be hingably attached. In some configurations, the access panel 144 can be on a sidewall, the top, or the bottom.

The heating element 803, fan 807, and/or ion generator 805 can be connected to an electrical power source. The electrical power source can be connected via a power cord 148, as shown in FIG. 5, which can be connected by user to a wall socket. In other embodiments, the electrical power source can be one or more batteries (e.g., such that the dryer 100, 200 can operate on battery power and without requiring connection to a wall socket).

As illustrated in FIG. 8, the base of the enclosure 100 can include an optional drain 817 (e.g., a grate with a plurality of apertures) in the interior bottom surface 120 that allows the moisture from the wefted hair to be removed and separated from the interior components of the enclosure 100. Substantially all or most of the air and moisture can be ducted down and out of the enclosure 100. The drain 817 can optionally be a floor drain that is plumbed to the sewer system. In one embodiment, below the drain 817 can be a moisture capturing device 815 (e.g., tray, bucket) that can capture moisture removed from the wefted hair while in the enclosure. In some embodiments, the moisture capturing device 815 can be a container disposed in the bottom portion of the enclosure 100, where at least a portion of the moisture capturing device 815 is disposed below the wefted hair. In some embodiments, the moisture capturing device 815 is a removable container that collects the moisture removed from the wefted hair.

In some configurations, a drain 817 and/or moisture capturing device 815 can be excluded from the dryer 100, 200 because the wefted hair does not drip a substantial amount of water during the drying process (while in the enclosure 100). The conditions in the enclosure 100 are such that the excess moisture can be carried by the air and does not substantially accumulate on the interior surfaces of the enclosure.

Figure 6:
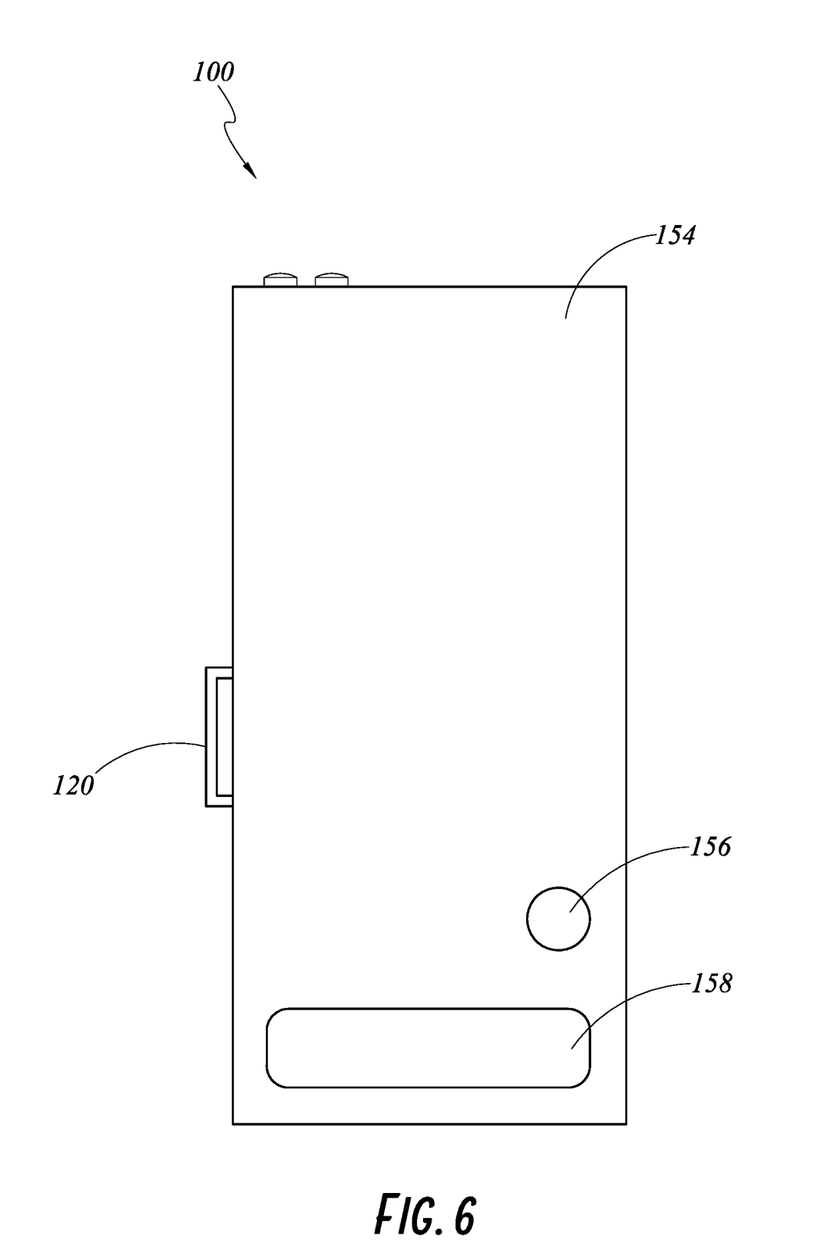
FIG. 6 is a side view of the dryer of FIG. 1A.

In some configurations, the enclosure can have one or more exhausts to exhaust air and/or moisture from the interior area/volume 811 of the dryer 100, 200. The exhaust(s) can be located on at least one wall of the enclosure (e.g., front, left, right, and/or rear). Preferably, the exhaust 158 is located on the lower half of a side wall 154, as illustrated in FIG. 6. The exhaust can have any suitable size, shape, and location. The size, shape, and location of the exhaust can depend on the heating element 803 and/or fan 807 used.

In some configurations, the enclosure can have one or more intakes to allow air to flow into the dryer 100, 200 and be in communication with the heating element 803 and/or fan 807. The intake(s) can be located on at least one wall of the enclosure (e.g., front, left, right, and/or rear). Preferably, the intake 156 is located on a sidewall 154, as illustrated in FIG. 6. The intake 156 can have any suitable size, shape, and location. The size, shape, and location of the intake can depend on the heating element 803 and/or fan 807 used. There can be a filter or screen over the intake 156 to inhibit the intake of debris (e.g., hair or other large particles).

In some embodiments, the enclosure 100 can have an optional interior lining 813, as illustrated in FIG. 8. The lining 813 can line at least part of the interior of the enclosure 100. As illustrated in FIG. 8, the lining 813 can at least partially line an interior back wall 116. In some embodiments, the lining 813 can at least partially line one or more interior walls of the enclosure 100 (e.g., left 118, right, top, bottom 120, back 116, and/or front). In some embodiments, the lining 813 can at least partially line the inside of the door 102. The lining 813 can be made of a heat resistant material, such that it will not melt and/or emit fumes that could be absorbed by the wefted hair. The lining can help the enclosure retain heat. In some embodiments, one or more interior surfaces of the enclosure are at least partially lined with a heat resistant material. In one embodiment, the heat resistant material can be a High Density Polyethylene (HDPE) material made by Interstate Plastics of Downey, Calif. In some embodiments, one or more interior surfaces of the enclosure can be made of a coated metal. In some embodiments, the lining 813 can be made of a coated metal.

The dryer can be formed from any suitable materials keeping in mind that the enclosure will handle air that is at least about 115 degrees Fahrenheit. In some instances, the dryer will handle air that is between about 180 and about 200 degrees Fahrenheit. Preferably, the dryer is formed of a material that can tolerate air temperatures below about 240 degrees Fahrenheit. Using a plastic material to form the dryer can provide insulating properties. In addition, the thickness of the walls can help insulate the dryer. The dryer can be made from wood, glass, plastic, stainless steel, aluminum, metal, or other suitable material. The dryer may be visible in the salon such that materials can be visually appealing.

The dryer can have a plurality of legs or a support structure. The bottom of the dryer can be elevated off the ground. The bottom of the dryer can include casters, wheels, or the like to facilitate moving the dryer.

Method of Drying Wefted Hair

The wefted hair can be shampooed and/or combed out before it is ready to be dried. Before being placed in the enclosure, the wefted hair can be patted dry with a towel. By patting the wefted hair with a towel, the amount of moisture in the enclosure can be reduced. The wefted hair is hung on one or more tines in the enclosure. Preferably, the wefted hair does not touch the bottom of the enclosure to provide airflow around the wefted hair.

In some instances, the wefted hair can be processed, such as coloring or another chemical process, before being placed in the enclosure. Some processes require heat. Processed wefted hair can be placed on a tray in the enclosure. Colored wefted hair can be placed on a tray so that the dye does not drip off the hair.

In some instances, the drying of wefted hair can include wefted hair be hung on one or more tines and processed wefted hair placed on one or more trays. In some instances, drying hung wefted hair is done separately from drying processed wefted hair in trays.

In some instances, a temperature level can be selected. The temperature can range from 0° F. to 240° F. Preferably, the temperature is set to about 200° F., which is a temperature that should not damage the hair.

In some instances, a fan level can be selected. The fan speed can vary. Preferably, the fan can have three speeds. The fan speed can affect how the fast the heated air flows through the enclosure.

In some instances, an ion generator can be used to create negative ions, which help soften the hair. In some instances, a UV light can be used to help sterilize the hair. In some instances, a humidity sensor is used to determine the humidity level in the enclosure.

In some instances, a timer is set, such that the fan and/or heating element are shut off once a selected time has been reached. In some instances, a timer is set, such that the UV light and/or ion generator are shut off once a selected time has been reached. In some instances, there may be a visual and/or audible alert notifying the user that the selected time has been reached.

In some instances, a controller 823 can be used to shut on or off the heating element and/or fan, once a selected temperature has been reached. This can be used to prevent the enclosure from getting too cold or too hot. In some instances, a controller 823 can be used to shut on or off the heating element and/or fan once a selected humidity level has been reached. Having a minimum humidity level in the enclosure can prevent the hair from becoming too dry and damaged. However, a high humidity level can indicate that more moisture needs to be removed from the enclosure and wefted hair. There can be a visual and/or audible alert notifying the user that the selected temperature and/or humidity level has been reached.

The terms "approximately," "about," and "substantially" as used herein represent an amount close to the state amount that still performs a desired function or achieves a desired result. For example, in some embodiments, as the context may dictate, the terms "approximately," "about," and "substantially" may refer to an amount that is within less than or equal to 10% of the stated amount. The term "generally" as used herein represents a value, amount, or characteristic that predominantly includes, or tends toward, a particular value, amount, or characteristic. As an example, in certain embodiments, as the context may dictate, the term "generally parallel" can refer to something that departs from exactly parallel by less than or equal to 20 degrees and/or the term "generally perpendicular" can refer to something that departs from exactly perpendicular by less than or equal to 20 degrees.

Some embodiments have been described in connection with the accompanying drawings. The figures are drawn to scale, but such scale should not be interpreted to be limiting. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Also, any methods described herein may be practiced using any device suitable for performing the recited steps.

Although the present invention has been described in terms of a certain embodiment, other embodiments apparent to those of ordinary skill in the art also are within the scope of this invention. Thus, various changes and modifications may be made without departing from the spirit and scope of the invention. For instance, various components may be repositioned as desired. Moreover, not all of the features, aspects and advantages are necessarily required to practice the present invention. Accordingly, the scope of the present invention is intended to be defined only by the claims that follow.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a sub combination.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A system for drying wefted hair comprising:
   an enclosure configured to allow a flow of air and moisture through the enclosure;
   a rack having a plurality of tines positioned within the enclosure;
   a heating element configured to heat air that flows into the enclosure;
   an ion generator configured to supply negative ions into the enclosure;
   a fan configured to direct heated air through the enclosure; and
   a controller configured to control an operational setting of one or more of the heating element, the ion generator, and the fan,
   wherein the wefted hair can be hung from the tines of the rack in the enclosure, and one or both of the fan and the heating element are operable to heat the air in the enclosure to remove moisture from the wefted hair to dry the wefted hair.

2. The system of claim 1, further comprising a timer electrically connected to the controller the controller configured to automatically shut off power to one or both of the heating element and the fan a preselected time set on the timer has been reached.

3. The system of claim 1, wherein one or more of the heating element, the controller, the ion generator, and the fan are disposed away from the rack to inhibit contact with moisture that is removed from the wefted hair.

4. The system of claim 3, wherein one or more of the heating element, the controller, the ion generator, and the fan are disposed in a compartment within the enclosure.

5. The system of claim 1, wherein the heating element is operable to a maximum temperature of about 200° F.

6. The system of claim 1, wherein the ion generator is a 30 diode ion generator.

7. The system of claim 1, further comprising one or more sensors configured to sense a parameter in the enclosure and to communicate a signal corresponding to a sensed information in the enclosure to the controller, the controller configured to control the operation of one or both of the heating element and the fan based at least in part on the sensed information signals from the one or more sensors.

8. The system of claim 7, wherein the one or more sensors comprises a temperature sensor.

9. The system of claim 7, wherein the one or more sensors comprises a humidity sensor.

10. The system of claim 1, wherein one or more interior surfaces of the enclosure are at least partially lined with a heat resistant material.

11. The system of claim 1, wherein the rack is attached to an interior wall of the enclosure.

12. The system of claim 1, wherein the rack is attached to a door of the enclosure, the door movable between open and closed positions relative to an opening of the enclosure.

13. The system of claim 1, further comprising a tray removably positionable within the enclosure, the tray configured to hold processed wefted hair.

14. The system of claim 1, wherein a width of the enclosure is between about 10 inches and about 20 inches, a height of the enclosure is between about 20 inches and 40 inches, and a depth of the enclosure is between about 10 inches and 20 inches.

15. The system of claim 1, wherein the rack has a length of between about 6 inches and 36 inches.

16. The system of claim 1, wherein each of the tines has a diameter of between about 0.06 inches and 0.12 inches.

17. The system of claim 14, wherein a space between the tines is between about 0.1 inches and about 1 inch wide.

18. The system of claim 1, wherein a position of the rack within the enclosure is adjustable.

19. The system of claim 1, further comprising an ultraviolet light source configured to direct ultraviolet light within the enclosure to sterilize the wefted hair.

20. The system of claim 1, further comprising a moisture capturing device configured to capture moisture removed from the wefted hair while in the enclosure.

* * * * *